United States Patent
Ohno et al.

(10) Patent No.: US 6,967,260 B2
(45) Date of Patent: Nov. 22, 2005

(54) METHOD FOR PURIFICATION OF TETRAFLUOROMETHANE AND USE THEREOF

(75) Inventors: Hiromoto Ohno, Kawasaki (JP); Toshio Ohi, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 630 days.

(21) Appl. No.: 10/019,137

(22) PCT Filed: Apr. 26, 2001

(86) PCT No.: PCT/JP01/03664

§ 371 (c)(1),
(2), (4) Date: Dec. 27, 2001

(87) PCT Pub. No.: WO01/83412

PCT Pub. Date: Nov. 8, 2001

(65) Prior Publication Data

US 2003/0034309 A1 Feb. 20, 2003

Related U.S. Application Data

(60) Provisional application No. 60/230,704, filed on Sep. 7, 2001.

(30) Foreign Application Priority Data

Apr. 28, 2000 (JP) ........................................ 2000-128681

(51) Int. Cl.$^7$ ..................... C07C 17/389; C07C 17/38
(52) U.S. Cl. ..................... 570/179; 570/161; 570/164; 570/170; 570/177
(58) Field of Search ......................... 570/179, 161, 570/164, 170, 177

(56) References Cited

U.S. PATENT DOCUMENTS 3,026,359 A   3/1962   Mastrangelo et al.
5,417,742 A   5/1995   Tamhankar et al.

OTHER PUBLICATIONS

Patent Abstract of Japan, vol. 1996, No. 07, Jul. 31, 1996 & JP 08 081399 A (SHOWA DENKO KK), Mar. 26, 1996 cited in the application abstract.

*Primary Examiner*—Elvis O. Price
(74) *Attorney, Agent, or Firm*—Sughrue Mion, PLLC

(57) ABSTRACT

Tetrafluoromethane containing ethylene compound, hydrocarbon compounds, carbon monoxide and/or carbon dioxide is contacted with zeolite having an average pore size of 3.4 to 11 Å and an Si/Al ratio of 1.5 or less and/or a carbonaceous adsorbent having an average pore size of 3.4 to 11 Å. Thus, high-purity tetrafluoromethane can be obtained which is advantageous in industry and provides good profitability.

14 Claims, No Drawings

METHOD FOR PURIFICATION OF TETRAFLUOROMETHANE AND USE THEREOF

CROSS-REFERENCE TO RELATED APPLICATION

This application is an application filed under 35 U.S.C. § 111(a) claiming benefit pursuant to 35 U.S.C. § 119(e)(1) of the filing date of the Provisional Application 60/230,704 filed Jul. 9, 2000, pursuant to 35 § 111(b).

TECHNICAL FIELD

The present invention relates a method for the purification of tetrafluoromethane (hereinafter it may be referred to as "FC-14" or "$CF_4$") and a use of the purified tetrafluoromethane.

BACKGROUND ART

FC-14 is used as an etching gas or a cleaning gas in, for example, the manufacturing of semiconductor devices, therefore, a high-purity product thereof is demanded.

For the production of FC-14, various methods have heretofore been proposed. Specifically the following methods, for example, are known:

(1) a method of reacting dichlorodifluoromethane with hydrogen fluoride in the presence of a catalyst;

(2) a method of reacting monochlorotrifluoromethane with hydrogen fluoride in the presence of a catalyst;

(3) a method of reacting trifluoromethane with fluorine gas;

(4) a method of reacting carbon with fluorine gas; and (5) a method of thermally decomposing tetrafluoroethylene.

However, these methods for producing FC-14 have a problem in that intermediates of FC-14 or by-products produced by the reaction or impurities derived from raw materials form an azeotropic mixture or an azeotrope-like mixture with the objective FC-14 and the separation thereof is extremely difficult. To cope with this, for example, a purification method for treating FC-14 containing trifluoromethane ($CHF_3$), as an impurity, with zeolite or a carbonaceous adsorbent has been proposed (see, Japanese Patent No. 2,924,660).

DISCLOSURE OF INVENTION

Heretofore, however, an industrially advantageous method has not been known where FC-14 containing ethylene compounds, hydrocarbon compounds, carbon monoxide and/or carbon dioxide, as impurities, is purified and thereby high-purity FC-14 almost free of these impurities can be obtained with good profitability.

The present invention has been made under these circumstances and the object of the present invention is to provide a purification method where FC-14 is contacted with an adsorbent to remove by adsorption those impurities and whereby high-purity FC-14 can be obtained in an industrially advantageous manner with good profitability.

As a result of extensive investigations to solve the above-described problems, the present inventors have found that, in a process for producing high-purity FC-14, when FC-14 containing ethylene compounds, hydrocarbon compounds, carbon monoxide and/or carbon dioxide, as impurities, is contacted with An adsorbent comprising zeolite having a specific average pore size and a specific Si/Al ratio and/or a carbonaceous adsorbent (Molecular Sieving Carbon) having a specific average pore size, the impurities can be selectively adsorbed and removed and high-purity FC-14 almost free of impurities can be obtained. The present invention has been accomplished based on this finding.

Thus, the present invention provides a method for the purification of tetrafluoromethane and use of the purified tetrafluoromethane, described in (1) to (15) below.

(1) A method for the purification of tetrafluoromethane, comprising contacting tetrafluoromethane containing one or more ethylene compounds, one or more hydrocarbon compounds, carbon monoxide and/or carbon dioxide, as impurities, with zeolite having an average pore size of 3.4 to 11 Å and an Si/Al ratio of 1.5 or less and/or a carbonaceous adsorbent having an average pore size of 3.4 to 11 Å to reduce the amount of the impurities.

(2) The method as described in (1) above, wherein tetrafluoromethane containing the impurities is contacted with zeolite and/or the carbonaceous adsorbent in a liquid phase.

(3) The method as described in (1) or (2) above, wherein zeolite is at least one selected from the group consisting of MS-4A, MS-5A, MS-10X and MS-13X.

(4) The method as described in (1) or (2) above, wherein the carbonaceous adsorbent is Molecular Sieving Carbon 4A and/or Molecular Sieving Carbon 5A.

(5) The method as described in any one of (1) to (4) above, wherein the one or more ethylene compounds are selected from the group consisting of ethylene, fluoroethylene, difluoroethylene and tetrafluoroethylene.

(6) The method as described in (5) above, wherein the one or more ethylene compounds are ethylene and/or tetrafluoroethylene.

(7) The method as described in any one of (1) to (4) above, wherein the one or more hydrocarbon compounds are selected from the group consisting of methane, ethane and propane.

(8) The method as described in (7) above, wherein the one or more hydrocarbon compounds are methane and/or ethane.

(9) The method as described in any one of (1) to (8) above, wherein the total content of the one or more ethylene compounds, the one or more hydrocarbon compounds, carbon monoxide and carbon dioxide contained in the tetrafluoromethane is reduced to 3 ppm or less.

(10) The method as described in any one of (1) to (9) above, wherein the tetrafluoromethane containing one or more ethylene compounds, one or more hydrocarbon compounds, carbon monoxide and/or carbon dioxide as impurities is produced by a direct fluorination method of reacting trifluoromethane with fluorine gas.

(11) The method as described in any one of (1) to (9) above, wherein the tetrafluoromethane containing one or more ethylene compounds, one or more hydrocarbon compounds, carbon monoxide and/or carbon dioxide as impurities is produced by a direct fluorination method of reacting carbon with fluorine gas.

(12) A tetrafluoromethane product having a purity of 99.9997 mass % or more, which is obtained by performing the purification according to the method as described in any one of (1) to (11) above.

(13) An etching gas comprising the tetrafluoromethane product described in (12) above.

(14) A cleaning gas comprising the tetrafluoromethane product described in (12) above.

In summary, the prevent invention provides "a method for the purification of tetrafluoromethane, comprising contacting FC-14 containing one or more ethylene compounds, one or more hydrocarbon compounds, carbon monoxide and/or carbon dioxide, as impurities, with zeolite having an average pore size of 3.4 to 11 Å and an Si/Al ratio of 1.5 or less and/or a carbonaceous adsorbent having an average pore size of 3.4 to 11 Å to reduce the amount of the impurities", "a tetrafluoromethane product having a purity of 99.9997 mass % or more, which is obtained by performing the purification according to the above-described method", and "an etching gas and a cleaning gas containing the above-described tetrafluoromethane product".

BEST MODE FOR CARRYING OUT THE INVENTION

For producing FC-14, for example, a method of reacting trifluoromethane with fluorine gas, a method of reacting carbon with fluorine gas and a method of thermally decomposing tetrafluoroethylene are known. When these methods are used, FC-14 obtained contains one or more ethylene compounds, one or more hydrocarbon compounds, carbon monoxide and/or carbon dioxide, as impurities, due to impurities in the raw materials, for example, organic trace impurities, trace oxygen, trace water content or the like.

The ethylene compounds contained may be one or more compounds selected from ethylene ($CH_2=CH_2$), monofluoroethylene ($CH_2=CHF$), difluoroethylene ($CH_2=CF_2$) and tetrafluoroethylene ($CF_2=CF_2$).

The hydrocarbon compounds contained may be one or more compounds selected from methane ($CH_4$), ethane ($C_2H_6$) and propane ($C_3H_6$).

The boiling points of the objective FC-14 and those impurities under atmospheric pressure are shown in Table 1 below.

TABLE 1

| Compound Name | Chemical Formula | Boiling Point (° C.) |
|---|---|---|
| Carbon monoxide | CO | −191.5 |
| Methane | $CH_4$ | −161.5 |
| FC-14 | $CF_4$ | −128 |
| Ethylene | $CH_2=CH_2$ | −103.7 |
| Ethane | $CH_3CH_3$ | −89 |
| Difluoroethylene | $CH_2=CF_2$ | −83 |
| Carbon dioxide | $CO_2$ | −78.5 |
| Tetrafluoroethylene | $CF_2=CF_2$ | −76.3 |
| Monofluoroethylene | $CH_2=CHF$ | −72 |
| Propane | $CH_2CH_2CH_2$ | −42.1 |

These impurities are very difficult to separate by a distillation operation because the objective FC-14 forms an azeotrope-like mixture therewith or as seen from Table 1, the boiling points are approximated. To cope with this, in an ordinary distillation operation, the number of stages of the distillation tower is increased or the number of distillation towers is increased to reduce the impurities as much as possible, however, this is not profitable and, moreover, high-purity FC-14 almost free of these impurities can hardly be obtained.

In the present invention, for selectively adsorbing and removing these impurities in FC-14, zeolite having an average pore size of 3.4 to 11 Å and an Si/Al ratio of 1.5 or less and/or a carbonaceous adsorbent (Molecular Sieving Carbon) having an average pore size of 3.4 to 11 Å is used as the adsorbent. For measuring the average pore size, a gas adsorption process using Ar gas may be used.

Thus the adsorbent is (1) zeolite having an average pore size of 3.4 to 11 Å and an Si/Al ratio of 1.5 or less, (2) a carbonaceous adsorbent having an average pore size of 3.4 to 11 Å (Molecular Sieving Carbon) or (3) an adsorbent obtained by adding a carbonaceous adsorbent having an average pore size of 3.4 to 11 Å to zeolite having an average pore size of 3.4 Å; to 11 Å and an Si/Al ratio of 1.5 or less. The Si/Al ratio as used herein is an atomic ratio.

Specific examples of the impurities in FC-14, which can be removed by using these adsorbents, may be unsaturated compounds such as ethylene, monofluoroethylene, difluoroethylene and tetrafluoroethylene, hydrocarbon compounds such as methane, ethane and propane, and oxygen-containing compounds such as carbon monoxide and carbon dioxide. As the impurities, preferred are ethylene, tetrafluoroethylene, methane, ethane, carbon monoxide and carbon dioxide, and more preferred are ethylene and ethane.

The difference in the molecular size between the objective FC-14 and these impurities is small, therefore, selective adsorption and removal of the impurities in FC-14 can hardly be attained only by the difference in the molecular size. In the present invention, by taking account of polarity and pore size of the adsorbent, the following three kinds of adsorbents are used as an adsorbent which can selectively adsorb and remove the impurities.

The first adsorbent is zeolite having an average pore size of 3.4 to 11 Å and an Si/Al ratio of 1.5 or less. Specific examples thereof include MS-4A. MS-4A has an average pore size of about 3.5 Å and an Si/Al ratio of 1.0. By performing an adsorption operation using this zeolite, the contents of ethylene, tetrafluoroethylene, methane, ethane, carbon monoxide and carbon dioxide as impurities can be reduced. Depending on the kind of zeolite, the impurity content can be reduced even to 5 ppm or less and thereby, high-purity FC-14 can be obtained.

If zeolite having an average pore size of less than 3.4 Å, for example, a pore size of about 3.2 Å is used, a reduction in the impurity content cannot be verified, even where the Si/Al ratio is 1.5 or less.

Even when the Si/Al ratio is 1.5 or less, in the case of zeolite having an average pore size in excess of 11 Å, a reduction in the impurity content cannot be verified.

Furthermore, even when the average pore size is from 3.4 to 11 Å, in the case of zeolite having an Si/Al ratio in excess of 1.5, a reduction in the impurity content cannot be verified.

The second adsorbent is a carbonaceous adsorbent (Molecular Sieving Carbon) having an average pore size of 3.4 to 11 Å. For example, a carbonaceous adsorbent having an average pore size of about 4 Å, like the above-described zeolite, can reduce the impurity content to 5 ppm or less and thereby, high-purity FC-14 can be obtained.

However, in the case of a carbonaceous adsorbent having an average pore size in excess of 11 Å, reduction in the impurity content cannot be verified and, for example, in the case of activated carbon having an average pore size of about 35 Å, which is commonly used and exhibits strong adsorption activity, almost no reduction of impurities can be verified.

The third adsorbent is an adsorbent obtained by adding (mixing) a carbonaceous adsorbent (the second adsorbent) having an average pore size of 3.4 to 11 Å to zeolite (the first adsorbent) having an average pore size of 3.4 to 11 Å and preferably having an Si/Al ratio of 1.5 or less. Depending on the kind of this adsorbent, the impurity content can be reduced to even 3 ppm or less and thereby FC-14 having higher purity can be obtained. This is thought to occur because zeolite has an excellent function of adsorbing particularly carbon monoxide, carbon dioxide and the like, whereas the carbonaceous adsorbent has an excellent function of adsorbing particularly unsaturated compounds and the like, and when these two adsorbents are used in combination, an effect attributable to the combination use is brought out.

The above-described zeolite and carbonaceous adsorbent can be used alone but two or more kinds of the adsorbents may also be used in combination at a desired proportion. In the case of the third adsorbent, the mixing ratio between zeolite and the carbonaceous adsorbent may be varied according to the concentration of impurities.

The ethylene compounds, hydrocarbon compounds, carbon monoxide and/or carbon dioxide as impurities contained in PC-14 are not particularly limited on the concentration, however, the concentration is preferably 0.1 mass % or less, more preferably 0.05 mass % or less.

In the case where impurities other than those described above, for example, perfluorocompounds such as FC-116 ($CF_3CF_3$) and FC-218 ($C_3F_6$) are intermixed in the objective FC-14, the perfluorocompounds can be separated and removed by performing a distillation operation either before or after the step of treatment with the above-described adsorbent.

In the method for the purification of FC-14 according to the present invention, the method of contacting FC-14 containing impurities with an adsorbent is not limited and, for example, FC-14 containing impurities may be contacted with the adsorbent in a gaseous phase, by gas-liquid contacting or in a liquid phase. Among these, the method of contacting FC-14 containing impurities with the absorbent in a liquid phase is efficient and preferred.

For contacting FC-14 containing impurities with the adsorbent in a liquid phase, a known method such as batch system or continuous system may be used, however, industrially, a method of providing, for example, two units of fixed bed-type absorption towers may generally be employed and when one unit reaches its saturated adsorption limit, the other unit is then used and the first unit is subjected to regeneration.

At the time of contacting FC-14 containing impurities with an adsorbent, the treating temperature, the treated amount and the treating pressure are not particularly limited, however, the treating temperature is preferably low and suitably from −50° C. to +50° C. The treating pressure may suffice if, in the case of a liquid phase, the liquid phase can be maintained and in the case of a gaseous phase, the treating pressure is not particularly limited.

As described above, by using the purification method of the present invention, ethylene compounds, hydrocarbon compounds, carbon monoxide and/or carbon dioxide contained in FC-14 can be effectively adsorbed and removed and thereby high-purity FC-14 can be obtained. The purity of FC-14 obtained is 99.9997 mass % or more and for the analysis of FC-14 products having a purity of 99.9997 mass % or more, (1) gas chromatography (GC) using TCD method, FID method (each including the precut method) or ECD method, or (2) an analysis instrument such as gas chromatography mass spectrometer (GC-MS) may be used.

The obtained high-purity FC-14 can be used as an etching gas at the etching step in a process of producing a semiconductor device. Furthermore, the high-purity FC-14 can be used as a cleaning gas at a cleaning step in a process of producing a semiconductor device. In a production process of a semiconductor device such as LSI and TFT, a thin or thick film is formed using a CVD method, a sputtering method or a vapor deposition method and the film is etched to form a circuit pattern. In an apparatus for forming the thin or thick film, cleaning is performed to remove unnecessary deposits accumulated on the inner wall of the apparatus, jig and the like, because unnecessary deposits cause generation of particles and must be removed occasionally to produce a good-quality film.

In the etching by the use of FC-14, the etching may be performed under various dry etching conditions such as plasma etching and microwave etching, and FC-14 may be used by mixing it with an inert gas such as He, $N_2$ and Ar, or with a gas such as HCl, $O_2$ and $H_2$, at an appropriate proportion.

The present invention is further illustrated below by referring to the Examples and Comparative Examples, however, the present invention should not be construed as being limited to these examples.

Raw Material Example 1 of FC-14

Carbon was reacted with fluorine gas in the presence of a diluting gas, unreacted fluorine gas was removed, and the product gas rich in FC-14 was purified by fractional distillation according to a conventional method. Then, the product gas was analyzed by gas chromatography, as a result, the obtained FC-14 had the composition shown in Table 2 below.

TABLE 2

| Compound Name | Chemical Formula | Purity (mass %) |
| --- | --- | --- |
| FC-14 | $CF_4$ | 99.9688 |
| Carbon monoxide | CO | 0.0006 |
| Carbon dioxide | $CO_2$ | 0.0056 |
| Methane | $CH_4$ | 0.0012 |
| Ethylene | $CH_2\!=\!CH_2$ | 0.0112 |
| Tetrafluoroethylene | $CF_2\!=\!CF_2$ | 0.0028 |
| Ethane | $CH_3CH_3$ | 0.0099 |

Raw Material Example 2 of FC-14

Difluoromethane ($CH_2F_2$) was reacted with fluorine gas in the presence of a diluting gas, then the reacted gas was introduced into an alkali cleaning tower to remove hydrogen fluoride generated and the slight amount of unreacted fluorine gas. The product gas rich in FC-14 was purified by fractional distillation according to a known method and analyzed by gas chromatography, as a result, the obtained FC-14 had the composition shown in Table 3 below.

TABLE 3

| Compound Name | Chemical Formula | Purity (mass %) |
| --- | --- | --- |
| FC-14 | $CF_4$ | 99.9722 |
| Carbon monoxide | CO | 0.0005 |
| Carbon dioxide | $CO_2$ | 0.0025 |
| Methane | $CH_4$ | 0.0004 |
| Monofluoroethyene | $CH_2\!=\!CHF$ | 0.0056 |
| Difluoroethylene | $CH_2\!=\!CF_2$ | 0.0038 |
| Tetrafluoroethylene | $CF_2\!=\!CF_2$ | 0.0108 |
| Trifluoromethane | $CHF_3$ | 0.0042 |

EXAMPLE 1

Into a 200 ml stainless steel cylinder, 20 g of zeolite (Molecular Sieves 4A, produced by Union Showa K.K., average pore size; 3.5 Å, Si/Al ratio: 1) was filled and vacuum dried, then about 70 g of FC-14 of Raw Material Example 1 was filled while cooling the cylinder, and the contents were occasionally stirred while keeping the temperature at −20° C. After about 8 hours, the liquid phase part was analyzed by gas chromatography. The analysis results are shown in Table 4 below.

TABLE 4

| Compound Name | Chemical Formula | Purity (mass %) |
| --- | --- | --- |
| FC-14 | $CF_4$ | 99.9992 |
| Carbon monoxide | CO | <0.0001 |
| Carbon dioxide | $CO_2$ | <0.0001 |
| Methane | $CH_4$ | <0.0001 |
| Ethylene | $CH_2=CH_2$ | <0.0001 |
| Tetrafluoroethylene | $CF_2=CF_2$ | 0.0003 |
| Ethane | $CH_3CH_3$ | 0.0001 |

As is apparent from the results in Table 4, by using zeolite having an average pore size of 3.5 Å and an Si/Al ratio of 1 as the adsorbent, the amount of impurities in FC-14 can be reduced and the impurity content can be reduced to 10 ppm or less.

EXAMPLE 2

Into a 200 ml stainless steel cylinder, 20 g of zeolite (Molecular Sieves 13x, produced by Union Showa K.K., average pore size: 10 Å, Si/Al ratio: 1.23) was filled and vacuum dried, then about 70 g of FC-14 of Raw Material Example 1 was filled while cooling the cylinder, and the contents were occasionally stirred at room temperature (about 18° C.). After about 8 hours, the liquid phase part was analyzed by gas chromatography. The analysis results are shown in Table 5 below.

TABLE 5

| Compound Name | Chemical Formula | Purity (mass %) |
| --- | --- | --- |
| FC-14 | $CF_4$ | 99.9991 |
| Carbon monoxide | CO | <0.0001 |
| Carbon dioxide | $CO_2$ | <0.0001 |
| Methane | $CH_4$ | <0.0001 |
| Ethylene | $CH_2=CH_2$ | 0.0003 |
| Tetrafluoroethylene | $CF_2=CF_2$ | 0.0002 |
| Ethane | $CH_3CH_3$ | 0.0001 |

As is apparent from the results in Table 5, by using zeolite having an average pore size of 10 Å and an Si/Al ratio of 1.23 as the adsorbent, the amount of impurities in FC-14 can be reduced and the impurity content can be reduced to 10 ppm or less.

EXAMPLE 3

Into a 200 ml stainless steel cylinder, 20 g of carbonaceous adsorbent (Molecular sieving Carbon, produced by Takeda Yakuhin Kogyo K.K., average pore size: 4 Å) was filled and vacuum dried, then about 70 g of FC-14 of Raw Material Example 2 was filled while cooling the cylinder, and the contents were occasionally stirred at room temperature (about 18° C.). After about 8 hours, the liquid phase part was analyzed by gas chromatography. The analysis results are shown in Table 6 below.

TABLE 6

| Compound Name | Chemical Formula | Purity (mass %) |
| --- | --- | --- |
| FC-14 | $CF_4$ | 99.9992 |
| Carbon monoxide | CO | 0.0001 |
| Carbon dioxide | $CO_2$ | 0.0002 |
| Methane | $CH_4$ | 0.0001 |

TABLE 6-continued

| Compound Name | Chemical Formula | Purity (mass %) |
| --- | --- | --- |
| Monofluoroethylene | $CH_2=CHF$ | <0.0001 |
| Difluoroethylene | $CH_2=CF_2$ | <0.0001 |
| Tetrafluoroethylene | $CF_2=CF_2$ | <0.0001 |
| Trifluoromethane | $CHF_3$ | 0.0001 |

As is apparent from the results in Table 6, by using a carbonaceous adsorbent having an average pore size of 4 Å (Molecular sieving Carbon) as an adsorbent, the amount of impurities in FC-14 can be reduced and the impurity content can be reduced to 10 ppm or less.

EXAMPLE 4

Into a 200 ml stainless steel cylinder, 15 g of zeolite (Molecular Sieves 4A, produced by Uni on Showa K.K., average pore size: 3.5 Å, Si/Al ratio: 1) mixed with 15 g of a carbonaceous adsorbent (Molecular Sieving Carbon, produced by Takeda Yakuhin Kogyo K.K.: average pore size of 4 Å) was filled and vacuum dried, then about 70 g of FC-14 of Raw Material Example 1 was filled while cooling the cylinder, and the contents were occasionally stirred at room temperature (about 18° C.). After about 8 hours, the liquid phase part was analyzed by gas chromatography. The analysis results are shown in Table 7 below.

TABLE 7

| Compound Name | Chemical Formula | Purity (mass %) |
| --- | --- | --- |
| FC-14 | $CF_4$ | 99.9994 |
| Carbon monoxide | CO | <0.0001 |
| Carbon dioxide | $CO_2$ | <0.0001 |
| Methane | $CH_4$ | <0.0001 |
| Ethylene | $CH_2=CH_2$ | <0.0001 |
| Tetrafluoroethylene | $CF_2=CF_2$ | <0.0001 |
| Ethane | $CH_3CH_3$ | <0.0001 |

To determine the content of trace impurities, microanalysis was performed by gas chromatography using TCD method, FID method (including precut method) or ECD method, or by an analysis instrument such as gas chromatography mass spectrometer (GC/MS), and from the values obtained, the purity was calculated. The results are shown in Table 8.

TABLE 8

| Compound Name | Chemical Formula | Purity (mass %) |
| --- | --- | --- |
| FC-14 | $CF_4$ | 99.9998 |
| Carbon monoxide | CO | <0.4 ppm |
| Carbon dioxide | $CO_2$ | <0.4 ppm |
| Methane | $CH_4$ | <0.3 ppm |
| Ethylene | $CH_2=CH_2$ | <0.1 ppm |
| Tetrafluoroethylene | $CF_2=CF_2$ | <0.2 ppm |
| Ethane | $CH_3CH_3$ | <0.2 ppm |

As is apparent from the results in Table 8, the purity of the FC-14 obtained is 99.9997 mass % or more.

COMPARATIVE EXAMPLE 1

Into a 200 ml stainless steel cylinder, 20 g of zeolite (Molecular Sieves XH-9, produced by Union Showa K.K., average pore size: 3.2 Å, Si/Al ratio: 1) was filled and vacuum dried, then about 70 g of FC-14 of Raw Material Example 1 was filled while cooling the cylinder, and the contents were occasionally stirred at room temperature (about 18° C.). After about 8 hours, the liquid phase part was analyzed by gas chromatography. The analysis results are shown in Table 9 below.

TABLE 9

| Compound Name | Chemical Formula | Purity (mass %) |
|---|---|---|
| FC-14 | $CF_4$ | 99.9698 |
| Carbon monoxide | CO | 0.0004 |
| Carbon dioxide | $CO_2$ | 0.0051 |
| Methane | $CH_4$ | 0.0012 |
| Ethylene | $CH_2=CH_2$ | 0.0111 |
| Tetrafluoroethylene | $CF_2=CF_2$ | 0.0027 |
| Ethane | $CH_3CH_3$ | 0.0097 |

As is apparent from the results in Table 9, even when the Si/Al ratio is 1, if the average pore size of zeolite is less than 3.4 Å, almost no reduction in impurities can be verified.

COMPARATIVE EXAMPLE 2

Into a 200 ml stainless steel cylinder, 20 g of zeolite (H-ZSM-5, produced by N.E. Chemcat K.K., average pore size: 6 Å, Si/Al ratio: 75) was filled and vacuum dried, then about 70 g of FC-14 of Raw Material Example 1 was filled while cooling the cylinder, and the contents were occasionally stirred at room temperature (about 18° C.). After about 8 hours, the liquid phase part was analyzed by gas chromatography. The analysis results are shown in Table 10 below.

TABLE 10

| Compound Name | Chemical Formula | Purity (mass %) |
|---|---|---|
| FC-14 | $CF_4$ | 99.9733 |
| Carbon monoxide | CO | 0.0003 |
| Carbon dioxide | $CO_2$ | 0.0047 |
| Methane | $CH_4$ | 0.0009 |
| Ethylene | $CH_2=CH_2$ | 0.0098 |
| Tetrafluoroethylene | $CF_2=CF_2$ | 0.0021 |
| Ethane | $CH_3CH_3$ | 0.0089 |

As is apparent from the results in Table 10, even when the average pore size is 6 Å, if the Si/Al ratio of zeolite exceeds 1.5, almost no reduction of impurities can be verified.

COMPARATIVE EXAMPLE 3

Into a 200 ml stainless steel cylinder, 20 g of a carbonaceous adsorbent (activated carbon, Particulate SHIROSAGI KL, produced by Takeda Yakuhin Kogyo K.K., average pore size; 35 Å) was filled and vacuum dried, then about 70 g of FC-14 of Raw Material Example 2 was filled while cooling the cylinder, and the contents were occasionally stirred at room temperature (about 18° C.). After about 8 hours, the liquid phase part was analyzed by gas chromatography. The analysis results are shown in Table 11 below.

TABLE 11

| Compound Name | Chemical Formula | Purity (mass %) |
|---|---|---|
| FC-14 | $CF_4$ | 99.9795 |
| Carbon monoxide | CO | 0.0004 |
| Carbon dioxide | $CO_2$ | 0.0021 |
| Methane | $CH_4$ | 0.0003 |
| Monofluoroethylene | $CH_2=CHF$ | 0.0038 |
| Difluoroethylene | $CH_2=CF_2$ | 0.0026 |
| Tetrafluoroethylene | $CF_2=CF_2$ | 0.0079 |
| Trifluoromethane | $CHF_3$ | 0.0034 |

As is apparent from the results in Table 11, with a carbonaceous adsorbent having an average pore size in excess of 11 Å, reduction of impurities cannot be verified.

Industrial Applicability

According to the present invention, the amount of impurities contained in tetrafluoromethane which had been heretofore very difficult to remove, particularly ethylene compounds, hydrocarbon compounds, carbon monoxide and/or carbon dioxide can be reduced. The high-purity tetrafluoromethane, after purification, can be used as an etching gas or a cleaning gas.

We claim:

1. A method for the purification of tetrafluoromethane, comprising contacting tetrafluoromethane containing one or more ethylene compounds, one or more hydrocarbon compounds, carbon monoxide and/or carbon dioxide as impurities with zeolite having an average pore size of 3.4 to 11 Å and an Si/Al ratio of 1.5 or less and a carbonaceous adsorbent having an average pore size of 3.4 to 11 Å to reduce the amount of said impurities.

2. The method as claimed in claim 1, wherein tetrafluoromethane containing said impurities is contacted with zeolite and the carbonaceous adsorbent in a liquid phase.

3. The method as claimed in claim 1 or 2, wherein zeolite is at least one selected from the group consisting of MS-4A, MS-5A, MS-10X and MS-13X.

4. The method as claimed in claim 1 or 2, wherein the carbonaceous adsorbent is Molecular Sieving Carbon 4A and/or Molecular Sieving Carbon 5A.

5. The method as claimed in claim 1 or 2, wherein the one or more ethylene compounds are selected from the group consisting of ethylene, fluoroethylene, difluoroethylene and tetrafluoroethylene.

6. The method as claimed in claim 5, wherein the one or more ethylene compounds are ethylene and/or tetrafluoroethylene.

7. The method as claimed in claim 1 or 2, wherein the one or more hydrocarbon compounds are selected from the group consisting of methane, ethane and propane.

8. The method as claimed in claim 7, wherein the one or more hydrocarbon compounds are methane and/or ethane.

9. The method as claimed in claim 1 or 2, wherein the total content of the one or more ethylene compounds, the one or more hydrocarbon compounds, carbon monoxide and carbon dioxide contained in the tetrafluoromethane is reduced to 3 ppm or less.

10. The method as claimed in claim 1 or 2, wherein the tetrafluoromethane containing one or more ethylene compounds, one or more hydrocarbon compounds, carbon monoxide and/or carbon dioxide as impurities is produced by a direct fluorination method of reacting trifluoromethane with fluorine gas.

11. The method as claimed in claim 1 or 2, wherein the tetrafluoromethane containing one or more ethylene compounds, one or more hydrocarbon compounds, carbon monoxide and/or carbon dioxide as impurities is produced by a direct fluorination method of reacting carbon with fluorine gas.

12. A tetrafluoromethane product having a purity of 99.9997 mass % or more, which is obtained by performing the purification according to the method described in claim 1 or 2.

13. An etching gas comprising the tetrafluoromethane product described in claim 12.

14. A cleaning gas comprising the tetrafluoromethane product described in claim 12.

* * * * *